Figure 1:
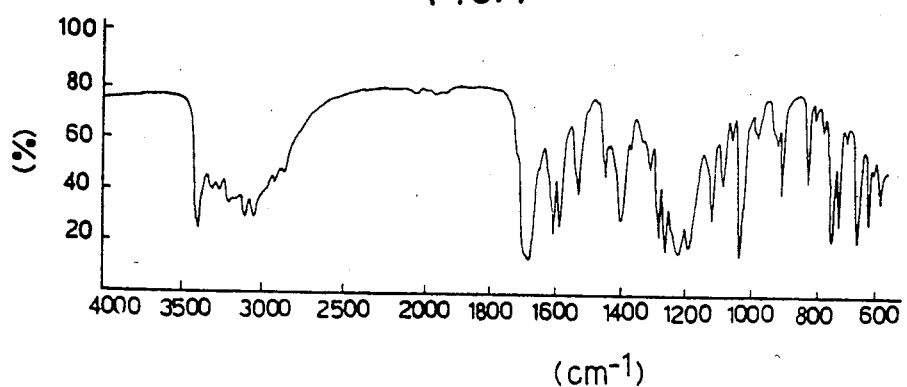

United States Patent [19]

Bruschi

[11] Patent Number: 4,577,019
[45] Date of Patent: Mar. 18, 1986

[54] STABILIZED ADDUCTS OF MENADIONE BISULFITE WITH P-AMINOBENZOIC ACID OR ADENINE

[75] Inventor: Enrico Bruschi, Genoa, Italy

[73] Assignee: Luigi Stoppani S.p.A., Milan, Italy

[21] Appl. No.: 518,769

[22] Filed: Aug. 2, 1983

Related U.S. Application Data

[63] Continuation of Ser. No. 273,379, Jun. 15, 1981, abandoned, which is a continuation of Ser. No. 102,445, Dec. 11, 1979, abandoned, which is a continuation-in-part of Ser. No. 971,031, Dec. 19, 1978, abandoned.

[30] Foreign Application Priority Data

Jul. 21, 1978 [IT] Italy ............................... 26008 A/78

[51] Int. Cl.$^4$ .................... C07D 473/34; C07C 49/66
[52] U.S. Cl. .................... 544/264; 544/333; 546/316; 546/318; 548/342; 548/372; 260/396 R; 260/396 K; 426/72
[58] Field of Search .............................. 546/316, 318; 260/396 R, 396 K; 548/342, 372; 544/333, 264; 424/266, 253, 251, 273 N

[56] References Cited

U.S. PATENT DOCUMENTS 2,367,302  1/1945  Moore et al. ........................ 424/331
3,328,169  6/1967  Nanninga ............................ 424/249

OTHER PUBLICATIONS

Moore, J. Am. Chem. Soc., vol. 63, pp. 2049 to 2051 (1941).
Baker et al., J. Am. Chem. Soc., vol. 64, pp. 1096 to 1101 (1942).
Okada, Chem. Abstracts, vol. 48, col. 5282 (1954).
Sullivan et al., Chem. Abstracts, vol. 53, Abst. on col. 1451 (1959).
Wang et al., Chem. Abstracts, vol. 55, Abst. bridging cols. 23928 to 23929 (1961).
Gstirner et al., Chem. Abstracts, vol. 62, Abst. bridging cols. 15996 to 15996.
Hata et al., Chem. Abstracts, vol. 68, Abst. 33121x (1968).
Chem. Abstracts, vol. 68, Subject Index E-O, p. 2506S (1969).
Ferkovich et al., Chem. Abstracts, vol. 76, Abst. 54,783v (1972).
Bellomonte et al., Chem. Abstracts, vol. 89, Abst. No. 89201z (1978).
Stoppani, Luigi S.p.A., Chem. Abstracts, vol. 92, Abst. No. 196897q.
Khalafallah et al., Chemical Abstracts, vol. 81, No. 12, Abst. No. 68,459-j, Sep. 23, 1974.
Neurath, The Proteins, Composition, Structure and Function, Second Edition, vol. III, pp. 178-181, Academic Press 1965.

Primary Examiner—Alan L. Rotman
Attorney, Agent, or Firm—Fleit, Jacobson, Cohn & Price

[57] ABSTRACT

Stabilized adducts of K vitaminic compounds, as menadione bisulfite or a derivative thereof and stabilizing vitamins as, particularly, nicotine amide or nicotinic acid. Feed compositions containing the same. Process for their preparation.

2 Claims, 7 Drawing Figures

STABILIZED ADDUCTS OF MENADIONE BISULFITE WITH P-AMINOBENZOIC ACID OR ADENINE

This application is a continuation of application Ser. No. 273,379, filed June 15, 1981 abandoned, which is a continuation of application Ser. No. 102,445 filed Dec. 11, 1979 now abandoned, which is a continuation in part application of Ser. No. 971,031 filed Dec. 19, 1978, now abandoned.

This invention relates to K vitaminic compounds and stabilizing vitamin adducts, consistent with K vitaminic compounds, as well as to the stabilized adducts thus obtained.

It relates also to the preparation of such adducts, particularly, to adducts stabilized with nicotine amide or nicotinic acid.

In another aspect, the present invention relates to composition for animal feed, containing the same as additives, as well as compositions for use in human therapy.

Particularly, the present invention relates to novel adducts of menadione bisulfite with compounds exhibiting vitaminic activity, such as for example, nicotinic acid and nicotine amide.

Adducts of menadione bisulfite have long been known, such as adducts of menadione sodium bisulfite (vitamin $K_3$). See U.S. Pat. No. 2,367,302. These adducts are water-soluble and have the substantial antihaemorrhagic activity of the K vitamin type and are not an irritant as menadione itself.

Menadione sodium bisulfite has been already widely used as an additive for feeds (particularly for poultry) and is also useful in the field of human therapy.

However, it suffers from the disadvantages of a limited stability to light, moisture, heat, and, particularly in a solution, having pH values higher than neutrality. Thus, the antihaemorrhagic activity of menadione or vitamin $K_3$, comprising the active principle thereof, will deteriorate in feed premixtures with the passage of time, and the products containing it do not stand up well in extended storage under unfavorable conditions.

In fact, it was shown (Baker et al J.A.C.S. 64 1096, 1942) that even at a relatively low pH (lower than neutrality), isomerization occurs resulting in a product which has no antihaemorrhagic activity. The rate of isomerization increases according to the pH of the medium, and at a pH of about 8.5, the adduct decomposes, releasing menadione.

Since feed premixtures may be moist and have a pH higher than neutrality, attempts were made to obviate the resulting unstability in such products by synthetizing the less water-soluble adducts of menadione bisulfite, not having the disadvantages of menadione sodium bisulfite. That is, they crystalized with 2-3 water molecules (thus promoting some solubility), and had a pH of 6.5 in saturated aqueous solutions, which is sufficiently high to promote a rather high rate of isomerization and accordingly a reduction in vitaminic activity.

Research in this direction resulted in the preparation of adducts of menadione bisulfite, wherein sodium was replaced by a slightly basic organic compound, particularly dicyanodiamidine, 2,4,6-triamino-1,3,5- triazine and pyrimidine substituted at position 2 (U.S. Pat. No. 3,328,169). These adducts had the characteristics supposedly useful for a stable menadione bisulfite apt to be introduced in feed premixtures (or for other uses), namely:

(1) absence of crystallization water
(2) low water-solubility; and
(3) pH of saturated solutions preferably lower than about 4.5.

The most accepted among these adducts is menadione pyrimidinole bisulfite (menadione-bisulfite-2-hydroxy-4,6-dimethyl-pyrimidine)(MPB).

In this adduct the amount of menadione is 45.63% by weight, and the amount of dimethyl pyrimidinole is 32.63% by weight. It is supposed that the basic portion of the MPB molecule enhances the $K_3$ vitaminic activity. However, it suffers from two disadvantages. First, although MPB is a pyrimidinic compound similar to natural pyrimidines, which are generally metabolized by an organism, it is not known how this synthetic product is metabolized. Second, its high proportion in the final product, in which it performs only the function of a stabilizer, leaves a high percentage of the product "inert" with respect to therapeutic activity.

Therefore, the present invention, on the one hand, eliminates the high proportion of an inert component, and, on the other hand, introduces a further component having a useful vitaminic activity which adds to that of the K vitaminic compound.

The products according to the present invention are adducts of menadione bisulfite with compounds, also having vitaminic activity, and at the same time having stabilizing properties with respect to the former. These adducts are the products of an addition reaction, producing an actual vitaminic unit or complex having a combined activity, and thus offering both the economic advantage of reduced cost due to the absence of an inert component possessing no vitaminic activity and the technical advantage, a surprisingly more active product. Thus, the present invention provides a unique product which combines a plurality of useful activities with an accompanying reduction in volume and handling otherwise required for obtaining the same results.

The products, according to the present invention, are obtained by reacting menadione sodium bisulfite or other highly water-soluble bisulfite adducts, such as potassium or ammonium adducts, with salts of e.g., nicotine amide or nicotinic acid in the presence of strong mineral acids, such as hydrochloric acid, sulphuric acid and phosphoric acid, or certain organic acids, such as acetic acid.

Preferably, the adducts are prepared by mixing concentrated solutions of menadione alkaline bisulfite with concentrated solutions of a salt of nicotine amide or nicotinic acid, such as chlorohydrate or sulphate, thus obtaining a precipitate which is easily separated by filtration.

Menadione itself could also be reacted with the bisulfite salt of nicotine amide or nicotinic acid; however, the reaction rate would be lower, and thus, the process is not preferred.

The adducts of menadione bisulfite with nicotine amide and nicotinic acid, as obtained according to the present invention, are free of water of crystallization and are slightly soluble in water and in an aqueous solution having a pH lower than 4.5 (maximum 3.0).

Because of their decomposition at a pH 8.5 in menadione and nicotine amide or nicotinic acid (sodium salt), the percentage of menadione is determined by the method shown in USA Pharmacopeia, 15th Edition, page 394.

The most preferred adduct of menadione bisulfite with nicotine amide has the general formula $C_{17}H_{16}O_6N_2S$, and a molecular weight of 376.42. It consists of:

Menadione: 45.74% by weight
Nicotine amide: 32.44% by weight

Its IR spectrum is shown in FIG. 1 (wave number in abscissa, $cm^{-1}$; in ordinate: transmittance (%)).

The most preferred adduct of menadione bisulfite with nicotinic acid has the general formula $C_{17}H_{15}O_7NS$, and a molecular weight of 377.36. It consists of:

Menadione: 45.62% by weight
Nicotinic acid: 32.62% by weight

Figure 2:
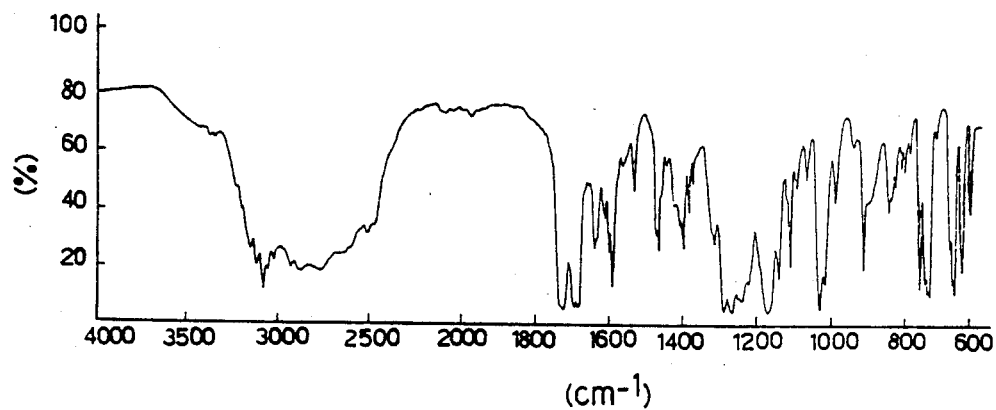

Its IR spectrum is shown in FIG. 2 (wave number and transmittance as in FIG. 1).

The adducts according to the present invention, when obtained as described, are particularly pure so as to be suitable for pharmaceutcal compositions intended for general antihaemorrhagic therapy.

In addition to the above, it was found that the addition of menadione bisulfite with other compounds also resulted in substances having excellent stability. This was particularly evident in compounds with vitaminic activity having a quaternizable nitrogen atom. These compounds can be grouped according to the following basic structures:

     (1)

The nitrogen atom in (1) may be part of a simple heterocyclic structure having one or more nitrogen atoms, for example, a penta- or hexa-atomic structure, or a complex structure comprising two or more condensed rings, which may be penta- or hexa-atomic aromatic or heterocyclic including N, S, O atoms; thus, for example, N may be part of a basic pyridinic ring structure

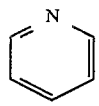

as in nicotine amide or nicotinic acid; a basic thiazolic ring structure

as in thiamine hydrochloride (vitamin $B_1$); and a purinic ring structure

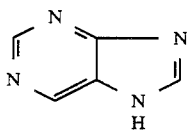

as in adenine hydrochloride (vitamin $B_4$); or

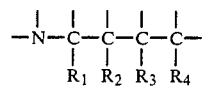     (2)

wherein —N is the quaternizable nitrogen atom. The sequence of carbon atoms in (2) forms part of an aliphatic or aromatic structure —$R_1$, $R_2$, $R_3$ and $R_4$ independently represent H, an aliphatic or aromatic radical, or a functional group.

Compounds of structure (2) would include, for example, aminobenzoic acids, particularly p-aminobenzoic acid, aliphatic and aromatic amines, for example, dibenzylethylenediamine. It would also include aminoacids, such as tryptophan(1-alpha-amino-3 indole propionic acid) or histidine(alpha-amino-4(or 5)-imidazole-propionic acid)($C_6H_9N_3O_2$)

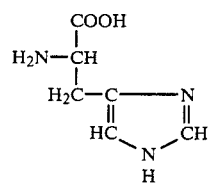

Another way of describing the adducts of the present invention is $KV_1(V_2)$, wherein K is the K-vitamin compound, $V_1$ is the stabilizing and therapeutically active component selected from the first group (1), e.g., nicotinic acid, nicotinic amide, vitamin $B_1$ and vitamin $B_4$; and $V_2$ is selected from the second group, e.g., aminobenzoic acid, histidine, and tryptophan. All the compounds ($V_1$, $V_2$) share the therapeutic activity of the new stabilized adducts of the invention.

For a better illustration of the present invention, the following examples are provided. These examples are illustrative of the present invention and should not be considered as limiting the same.

EXAMPLE I

A solution comprising 18.5 g nicotine amide and 150 ml 1N HCl was mixed with a solution of 50 g menadione sodium bisulfite in 100 ml of water at room temperature for about one hour. A white precipitate was obtained which, after filtering, washing and vacuum drying at 50°–60° C., weighed 48 g.

The product obtained is slightly soluble in water, m.p. 182°–183° C. with decomposition, and does not contain more than 1% water, as determined according to Karl Fischer's method, and its elementary analysis is as follows:

Actual: C=54.1%; H=4.1%; N=7.2%; S=8.2%
Theoretical for $C_{17}H_{16}O_6N_2S$: C=54.19%; H=4.25%; N=7.43%; S=8.52%

The percentage of menadione was 45.0%.

EXAMPLE II

A solution comprising 27 g of nicotine amide and 22 g of concentrated HCl (36%) in 120 ml water was admixed at room temperature with a solution comprising 25 g menadione sodium bisulfite in 75 ml water for about one hour. A precipitate of white color was obtained which, after filtering, washing and vacuum drying at 60° C., weighed 27 g.

The percentage of menadione was 45.2%. FIG. 1 shows the IR spectrum of this product, referred to as menadione nicotine amide bisulfite (MNB).

EXAMPLE III

A solution comprising 18.5 g nicotinic acid, 18 g concentrated HCl and 150 ml water was mixed at room temperature with an aqueous solution of menadione sodium bisulfite (50 g in 100 ml water). A white precipitate was obtained which, after filtration, washing and vacuum drying, weighed 47 g.

The product is slightly soluble in water; m.p. 184°–186° C. with decomposition; it is free of water of crystallization and contains 44.6% by weight of menadione and 33.5% by weight of nicotinic acid. FIG. 2 shows the IR spectrum of this product, referred to as menadione nicotinic acid bisulfite (MANB).

EXAMPLE IV

Menadione-bisulfite-p-amino benzoic acid adduct.

| Formula: | $C_{18}H_{17}O_7NS$ | M.W. = 391.4 |
|---|---|---|

10 g of p-amino benzoic acid were dissolved in 65 g of an 8.5% aqueous solution of hydrochloric acid. To this solution, 25 g of powdery menadione sodium bisulfite was added. After this addition, the solution was cooled to 5° C.; a white precipitate was obtained, which, after filtering, washing and vacuum drying, weighed 24 g.

| Analysis: | menadione | 42.5% |
|---|---|---|
| | p-aminobenzoic acid | 35.1% |
| | $H_2O$ | <1% |
| Water solubility | | 5.5 g/100 ml at 25° C. |
| pH (saturated solution) | | 1.8 |

Figure 3:
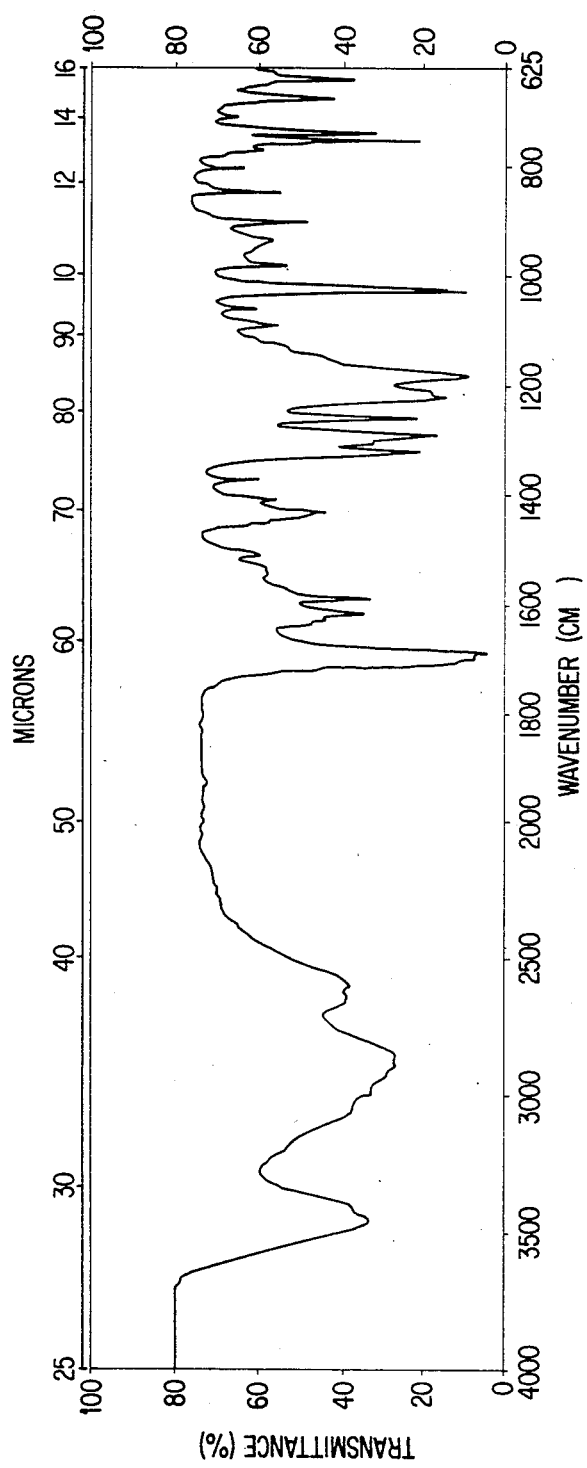

FIG. 3 shows the IR spectrum of this product.

EXAMPLE V

Menadione bisulfite-thiamine adduct.

| Formula: | $C_{23}H_{27}Cl\ N_4O_6S_2$ | M.W. = 555.17 |
|---|---|---|

25 g of thiamine hydrochloride (vitamin B$_1$) was dissolved in 50 g of water; to said solution of 25 g of powdery sodium menadione bisulfite was added within about half an hour. After half an hour of agitation, the reaction mass became opalescent and the adduct began to precipitate. After an hour, the precipitate was filtered, washed and dried. 25 g of a white product having the following analysis was obtained.

| Analysis: | menadione | 32.0% |
|---|---|---|
| | vitamin B$_1$ | 52.1% |
| | $H_2O$ | <1.0% |
| Water solubility | | 6.0 g/100 at 25° C. |
| pH (saturated solution) | | 2.7 |

Figure 4:
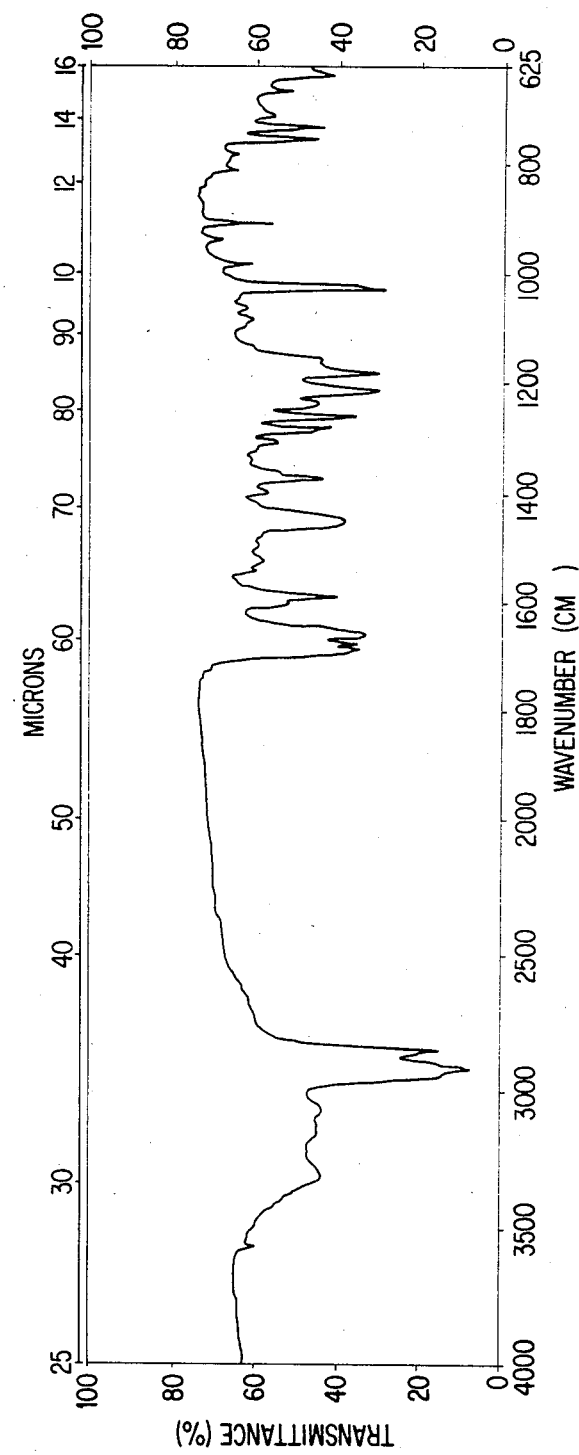

FIG. 4 shows the IR spectrum of this product.

EXAMPLE VI

Menadione bisulfite adenine adduct.

| Formula: | $C_{16}H_{15}N_5O_5S$ | M.W. = 389.42 |
|---|---|---|

10 g adenine was dissolved in a solution comprising 300 g of water and 8 g of concentrated 37% hydrochloric acid. To this solution, 25 g of powdery menadione sodium bisulfite was added. A white precipitate formed immediately. The slurry was filtered and washed. 29 g of a white granulated product having the following analysis was obtained.

| Analysis: | menadione | 43.2% |
|---|---|---|
| | adenine | 34.5% |
| | $H_2O$ | 0% |
| Water solubility | | 0.7 g/100 ml at 25° C. |
| pH (saturated solution) | | 3.3 |

Figure 5:
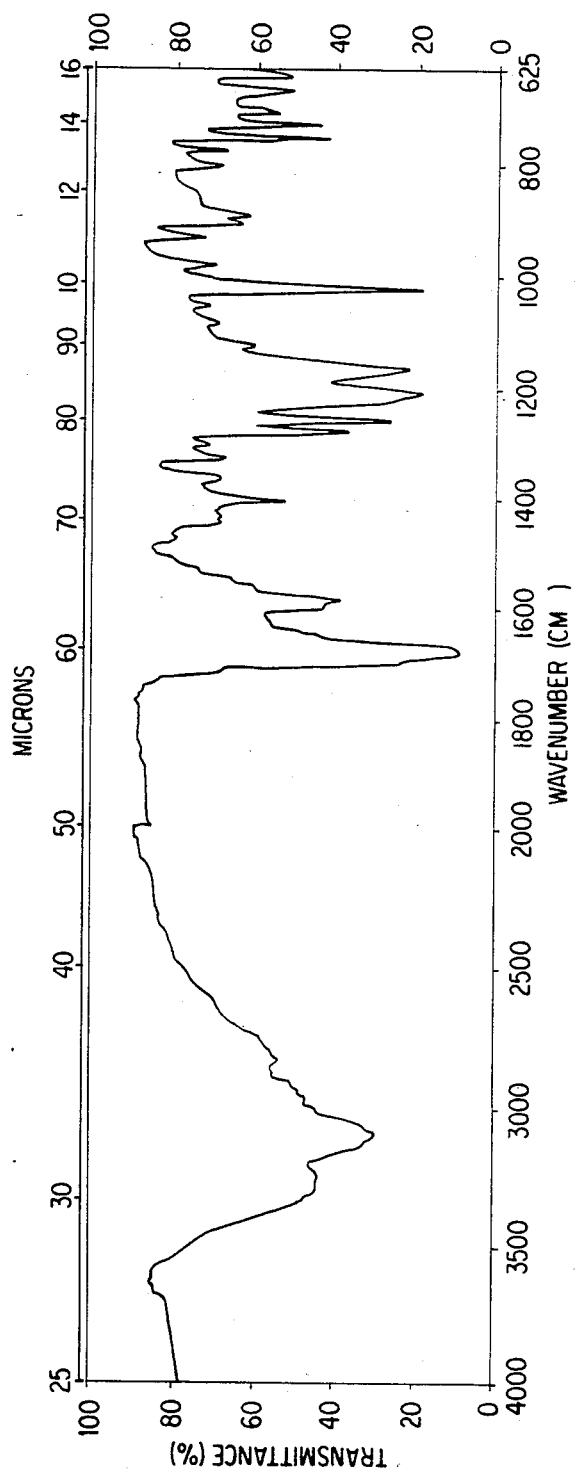

FIG. 5 shows the IR spectrum of this product.

EXAMPLE VII

Menadione bisulfite tryptophan adduct.

| Formula: | $C_{22}H_{22}N_2O_7S$ | M.W. = 458.51 |
|---|---|---|

15 g of tryptophan was dissolved in 70 g of a solution of 5% hydrochloric acid. To the resulting solution, 25 g of powdery menadione sodium bisulfite was added. The solution remained clear (under stirring) for about 1 hour. Afterwards, a white precipitate started forming; the precipitate, after filtering, washing and vacuum drying, weighed 25 g.

| Analysis: | menadione | 36.5% |
|---|---|---|
| | tryptophan | 44.2% |
| | $H_2O$ | <1.0% |
| Water solubility | | 1.7 g/100 ml at 25° C. |
| pH (saturated solution) | | 2.1 |

Figure 6:
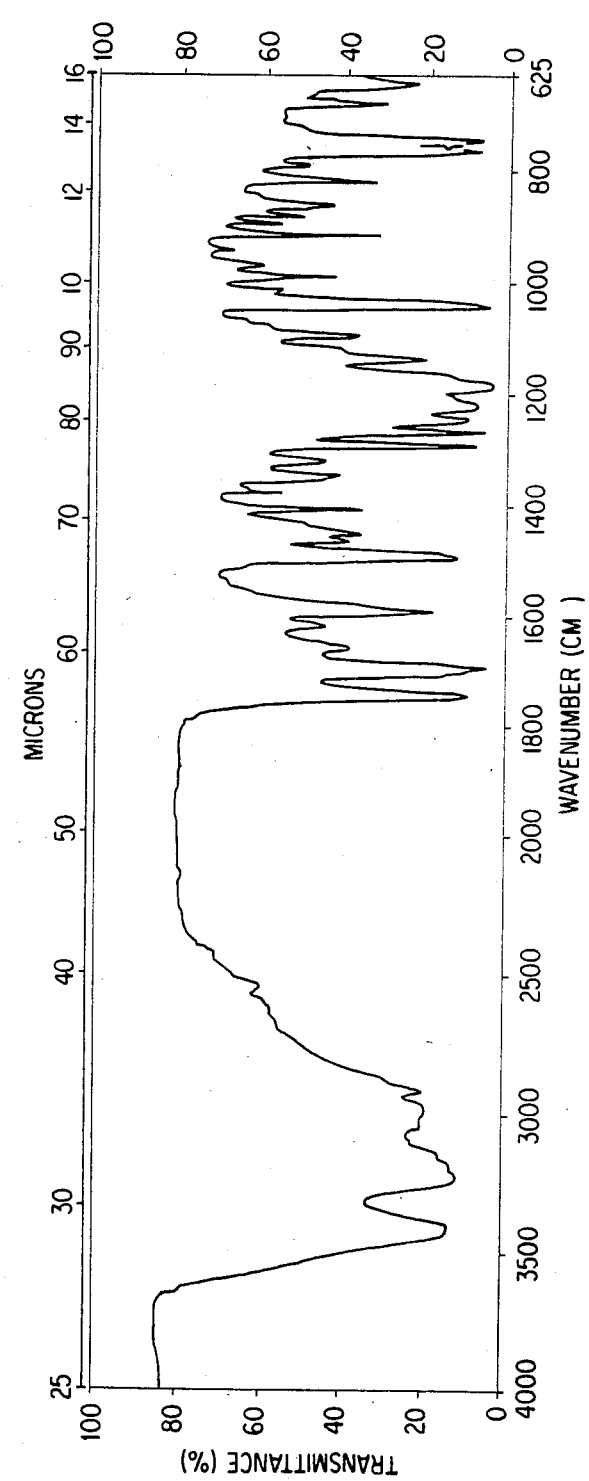

FIG. 6 shows the IR spectrum of this product.

EXAMPLE VIII

Menadione bisulfite-histidine adduct.

| Formula: | $C_{17}H_{19}N_3O_7S$ | M.W. = 409.45 |
|---|---|---|

16 g of histidine hydrochloride was dissolved in 50 g of a 6% solution of hydrochloric acid. To this solution, 25 g of powdery menadione sodium bisulfite was added within about ½ hour. A white, very fine precipitate was obtained, which, after filtering, washing and vacuum drying, weighed 26 g and had the following analysis:

| Analysis: | menadione | 41.2% |
|---|---|---|
| | histidine | 36.5% |
| | $H_2O$ | <1.0% |
| Water solubility | | 1.6 g/100 ml at 25° C. |
| pH (saturated solution) | | 2.1 |

Figure 7:
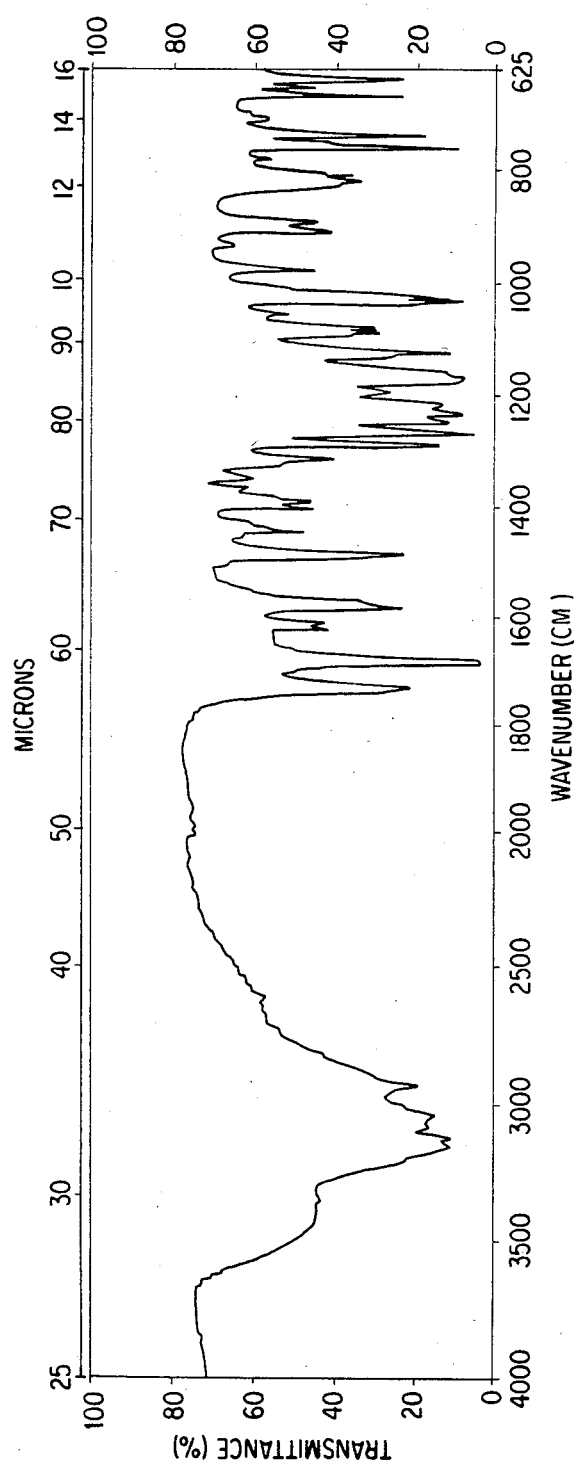

FIG. 7 shows the IR spectrum of this product.

EXAMPLE IX

Stabilization Test of Adduct With Nicotine Amide 1.5 g menadione bisulfite nicotine amide adduct, as prepared according to Example I, was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 75% of the original amount of menadione was still present.

EXAMPLE X

Stabilization Test Of Adducts With Nicotinic Acid 1.5 g adduct menadione nicotinic acid bisulfite (MANB) prepared according to Example III was mixed with 50 g aluminum silicate containing 11.25% moisture. The compound was placed in a sealed container and thermostatically maintained at 55° C. for 3 days. After this period, the percentage of menadione was determined according to the method of USA Pharmacopeia. 86% of the original amount of menadione was still present.

At the same time, tests were carried out under the same conditions, but using vitamin $K_3$ (menadione sodium bisulfite) and menadione bisulfite 2-hydroxy-4,6-dimethylpyrimidine adduct; in the former case, only 15.5% of the originally present menadione was unaltered, whereas in the latter case, the amount of unaltered menadione was 80.2%.

EXAMPLE XI

Stabilization Test Of Adduct With p-aminobenzoic acid 1.5 g menadione bisulfite p-aminobenzoic acid adduct as prepared according to Example IV was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 77% of the original amount of menadione was still present.

EXAMPLE XII

Stabilization Test of Adduct With Thiamine 1.5 g menadione bisulfite Thiamine adduct as prepared according to Example V was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 77% of the original amount of menadione was still present.

EXAMPLE XIII

Stabilization Test of Adduct With Adenine 1.5 g menadione bisulfite adenine adduct as prepared according to Example VI was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 95% of the original amount of menadione was still present.

EXAMPLE XIV

Stabilization Test of Adduct With Trypotophan 1.5 g menadione bisulfite tryptophan adduct, as prepared according to Example VII was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 85% of the original amount of menadione was still present.

EXAMPLE XV

Stabilization Test of Adduct With Histidine 1.5 g menadione bisulfite Histidine adduct, as prepared according to Example VIII was mixed with 50 g aluminum silicate, containing 11.25% moisture, determined according to Karl Fischer's method. The compound was placed in a sealed container and thermostatically maintained at 55° C. for 3 days. After this period, the percentage of menadione was determined according to the method described in USA Pharmacopeia. 63.5% of the original amount of menadione was still present.

EXAMPLE XVI

Preparation of Feeds

When preparing feeds, it is the standard practice to operate under dry and cold conditions. First, one prepares an active principle concentrate (a), which will be incorporated in the composition hereinafter shown at (b), which is a carrier for a feed integrator, thus obtaining a standard integrator. The standard integrator is diluted at time of use with the feeds suitable for each animal in the proper proportion.

Thus, for example, a typical integrator compound for feeds will contain, along with the carrier, the following composition of active ingredients.

| (a) Concentrate of active ingredients for kg of integrator | | | |
|---|---|---|---|
| ($a_1$) Commercial active concentrate without adduct | | ($a_2$) Active concentrate containing the adduct of the present invention | |
| Vitamin A | $10^6$ I.U. | Vitamin A | 3,500,000 I.U. |
| Vitamin $D_3$ | 200,000 I.U. | Vitamin $D_3$ | 400,000 I.U. |
| Vitamin $B_2$ | 1200 mg | Vitamin E | 3,500 mg |
| Vitamin $B_6$ | 600 mg | | |
| Vitamin $B_{12}$ | 1 mg | Vitamin $B_2$ | 400 mg |
| Vitamin PP | 2000 mg | Vitamin $B_{12}$ | 2 mg |
| Menadione sodium bisulphite (Vitamin $K_3$) | 2000 mg | Vitamin $B_6$ | 600 mg |
| | | Adduct of the invention (menadione nicotine amide bisulfite) | 4000 mg |
| (b) Carrier for feed integrator | | | |
| Maize flour | | | 400 g/kg |
| Soia bean flour | | | 200 g/kg |
| Rice flour | | | 100 g/kg |
| Purple medick flour | | | 100 g/kg |
| Peanut flour | | | 50 g/kg |
| Meat flour | | | 50 g/kg |
| Beet molasse | | | 25 g/kg |
| Barley flour | | | 25 g/kg |
| Dicalcium phosphate | | | 25 g/kg |
| Milled $CaCO_3$ | | | 15 g/kg |
| NaCl | | | 10 g/kg |

Then, amino-acids and mineral salts are added thereto.

The integrator thus obtained is in turn diluted in use with a specific feed suitable for the individual animals to which it is administered respectively.

As evident from the foregoing, by replacing the commercial concentrate ($a_1$) with a concentrate of active ingredients containing the adduct according to the present invention, the unstable vitamin $K_3$ and vitamin PP are replaced by a single stable product having the activity of both of said vitamins. This is clearly an advantage.

EXAMPLE XVII

Another example in which a compound according to the present invention is used in integrators for standard feeds:

| | |
|---|---|
| Vitamin A | 1,000,000 I.U. |
| Vitamin $D_3$ | 200,000 I.U. |
| Vitamin $B_2$ | 1,200 mg |
| Vitamin $B_{12}$ | 1 mg |
| Vitamin $B_6$ | 600 mg |
| Menadione nicotine amide bisulfite | 1,000 mg |

EXAMPLE XVIII

This example contemplates the product according to the invention in a concentrate for a treated integrator, that is, one provided with a specific therapeutic activity.

The composition of active concentrate for 1 kg of integrator corresponds to:

| | |
|---|---|
| Vitamin A | 3,000,000 I.U. |
| Vitamin E | 2,000 mg |
| Vitamin $B_2$ | 600 mg |
| Vitamin $B_{12}$ | 2 mg |
| Adduct according to the invention | 8,000 mg |

At the time of use, this kg of integrator is mixed with 100 kg standard feed.

What is claimed is:

1. Adducts of menadione bisulfite with p-aminobenzoic acid having the general formula: $C_{18}H_{17}O_7NS$, m.w. 391.4; menadione 42.5% by weight; p-aminobenzoic acid 35.1% by weight.

2. Adducts of menadione bisulfite with adenine having the general formula: $C_{16}H_{15}N_5O_5S$, m.w. 389.42; menadione 43.2% by weight; adenine 34.5% by weight.

* * * * *